United States Patent [19]

Fujita

[11] Patent Number: 4,655,708
[45] Date of Patent: Apr. 7, 1987

[54] ORTHODONTIC APPLIANCE

[76] Inventor: Kinya Fujita, 3998-5, Kamariya-cho, Kanazawa-ku, Yokohama-shi, Kanagawa-ken, Japan

[21] Appl. No.: 711,013

[22] Filed: Mar. 12, 1985

[30] Foreign Application Priority Data

Dec. 13, 1984 [JP] Japan ............................. 59-18449[U]

[51] Int. Cl.⁴ ................................................ A61C 7/00
[52] U.S. Cl. ......................................... 433/10; 433/17
[58] Field of Search ................................. 433/10, 8, 17

[56] References Cited

U.S. PATENT DOCUMENTS

| | | | |
|---|---|---|---|
| 2,921,371 | 1/1960 | Wallshein | 433/13 |
| 3,091,857 | 6/1963 | Rubin et al. | 433/11 |
| 4,184,254 | 1/1980 | Kraus | 433/17 |
| 4,354,833 | 10/1982 | Fujita | 433/20 |
| 4,371,333 | 1/1983 | Pletcher | 437/10 |

OTHER PUBLICATIONS

"Development of Lingual-Bracket Technique (Esthetic and Hygienic Approach to Orthodontic Treatment," Journal of the Japan Society for Dental Apparatus and Materials (vol. 19, No. 46, Apr. 1978).
"Multilingual-Bracket and Mushroom Arch Wire Technique," American Journal of Orthodontics, vol. 82, No. 2, pp. 120–140, Aug. 1982.
"Teeth Braces You Can't See," reprinted from Dental Clinical Reports, 1983.

Primary Examiner—Robert Peshock
Attorney, Agent, or Firm—Lowe, Price, LeBlanc, Becker & Shur

[57] ABSTRACT

The present invention relates to an arch wire holder, in orthodontic appliances, composed of a bracket which is fixed to a tooth and has a slot for receiving a wire and which supports a rotatable locking member which is rotatably engaged with the bracket to open and close the slot thereby permitting the wire to be secured to or detached from the slot. Using such a wire holder, attachment and detachment of arch wire can easily and positively be effected in a simple operation so that time required for dental treatment can be reduced, and medical accidents can be prevented.

9 Claims, 43 Drawing Figures

ORTHODONTIC APPLIANCE

BACKGROUND OF THE INVENTION

1. Field of the Invention

The present invention relates to a orthodontic appliance for the treatment of malocclusion, and more particularly to an improvement of a wire holder for receiving orthodontic arch wire.

2. Description of the Prior Art

Figure 21:
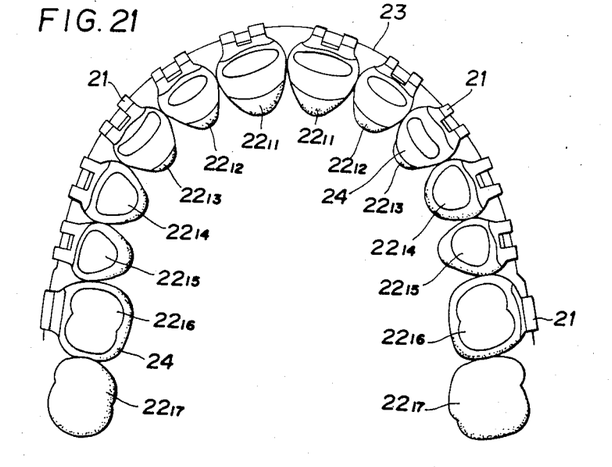
FIGS. 21 and 22 are explanatory views each showing a state wherein a conventional orthodontic appliance is attached to teeth.
Figures 22, 23:
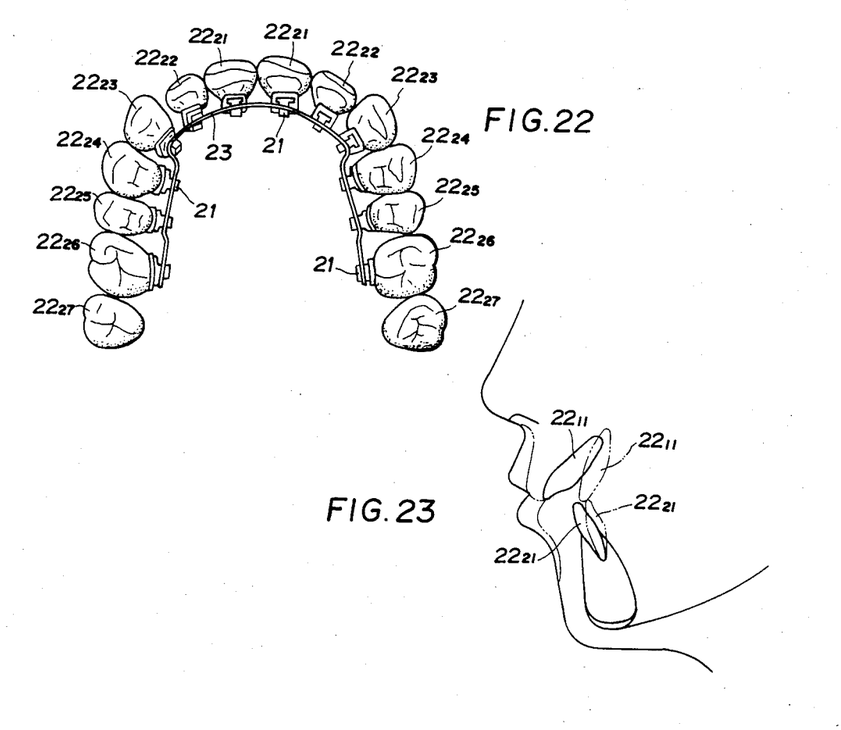
FIG. 23 is an explanatory view showing a row of teeth in human being.

In dental treatment involving the treatment of malocclusion as a major object, the newest and most highly developed method for correcting irregularities of the teeth is one in which brackets 21 constituting an arch wire holder are fixed to teeth 22, and a correcting wire 23 is successively inserted into these brackets 21 and is fixed so that malocclusion is corrected by elasticity of the arch wire 23 as illustrated in FIG. 21 or FIG. 23 (Japanese Utility Model Publication No. 44967/1982 filed by the present applicant). For example, as shown in FIG. 23, when central incisors $22_{11}$ of the upper jaw protruding outward abnormally as indicated by the solid line is to be corrected to have normal occlusion as indicated by the chain line, first, bands 24 are attached to the respective teeth $22_{11}$ and the brackets 21 are integrally welded to these bands 24 as shown in FIG. 21. Then one curved correcting arch wire 23 is successively fixed to these brackets 21, and its elasticity is utilized for the correction. In accordance with the method illustrated in FIG. 22, since the brackets are directly attached to the rear (lingual) side of teeth, the brackets 21 are invisible even when the mouth is opened, so that the mental burden of the patient can greatly be reduced.

For holding (fixing) a wire by means of a bracket (slot) in an orthodontic appliance for the treatment of malocclusion as described above, a method for tying up the wire to the bracket with a ligature, a method for fastening both the members with a pin, a method for securing both the members with a rubber band, and the like method have been proposed. These methods, however, require much time and labor in cases where many teeth must be treated. On the other hand, ligatures or pins which have been applied to the aforesaid members must be cut out when the wire is removed from the slots or brackets so that there is danger that cut pieces of the ligatures or pins spring may get into the patient's pharynx or larynx. Furthermore fixing (holding) of the wire by means of a rubber band imposes a limitation in the holding force, because of the mechanical properties of rubber material.

SUMMARY OF THE INVENTION

Accordingly objects of the present invention are to reduce the time required for orthodontic treatment, to prevent possible medical accidents, to positively hold an arch wire, and to make the attaching and detaching operations of such wire easy.

In accordance with the present invention, the above objects can be attained by an orthodontic appliance wherein a wire holder is fixed to each tooth, and at least one correcting (orthodontic) arch wire is successively engaged with each wire holder, for correcting irregularities of the teeth, comprising said wire holder being composed of a bracket to be fixed to a tooth and a rotatable member, said bracket having a slot for receiving said correcting arch wire, and said rotatable member being rotatably engaged with said bracket to open and close said slot, thereby readily permitting said wire to be attached to or detached from said slot.

DESCRIPTION OF THE EMBODIMENTS

Figure 1A:
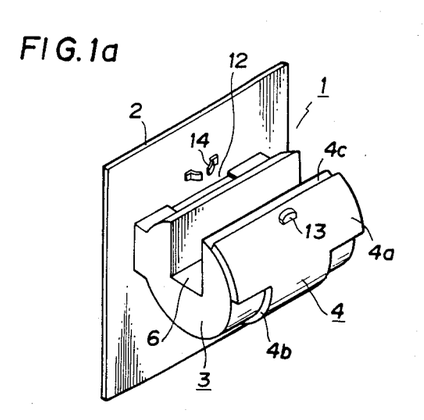
FIGS. 1a and 1b are a perspective view and a plan view respectively, each showing the opened state of an embodiment of the wire holder according to the present invention, and FIGS. 1c and 2d, likewise, are the respective sectional view and a plan view each showing the closed state of said wire holder.
Figure 1B:
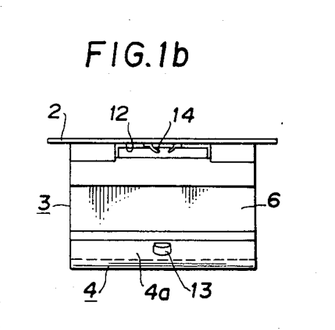
Figure 1C:
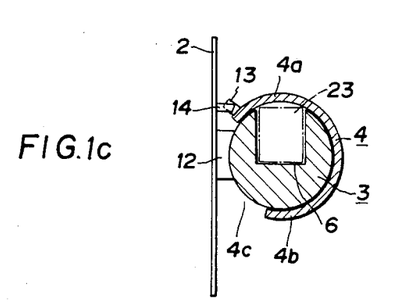
Figure 1D:
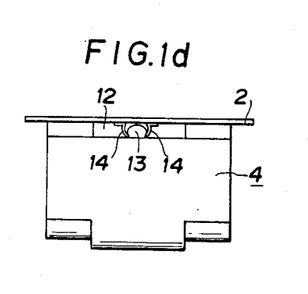

FIGS. 1a, 1b, 1c and 1d illustrate an embodiment of the present invention wherein an arch wire holder 1 for orthodontic appliance is composed of a bracket 3 constructed integral with to a stationary base 2 which is to be fixed directly to a tooth by adhesive bonding or other fixing means, and a rotatable member 4 for opening and closing a slot 6 provided in bracket 3 for inserting wire therein. As the stationary base 2, a plate-like member as in the present embodiment may be utilized in addition to the tooth-band as shown in FIG. 21. The bracket 3 has a cylindrical shape, along the whole length of which the groove-like slot 6 is axially defined for seating an arch wire 23 having a polygonal section. The rotatable member 4 is obtained by forming a plate-like member into a circular arc and it is rotatably and circumferentially engaged with the bracket 3 along the circumference thereof. The rotatable member 4 is constructed such that a part 4c thereof permits an opening of the slot 6 to open for receiving a wire 23 when the rotatable member 4 is in its opened position as shown in FIG. 1a. A portion 4a covers the opening of the slot 6 to capture the wire 23 when the rotatable member 4 is in its closed position as shown in FIGS. 1c and 1d. The rotatable member 4 consists of the cover portion 4a having a length substantially equal to that of the bracket 3 in the axial direction thereof and a body portion 4b which is adapted to be circumferentially movable through a guide hole 12 formed between the bracket 3 and the stationary base 2. The rotatable member 4 is optionally provided with an operating projection 13 on the outside surface thereof, whilst an engaging member 14 made of a leaf spring or the like is mounted on the stationary base 2 as shown in FIG. 1d for maintaining the rotatable member 4 at the closed position by engagingly or elastically fastening the operating projection 13.

Figure 2A:
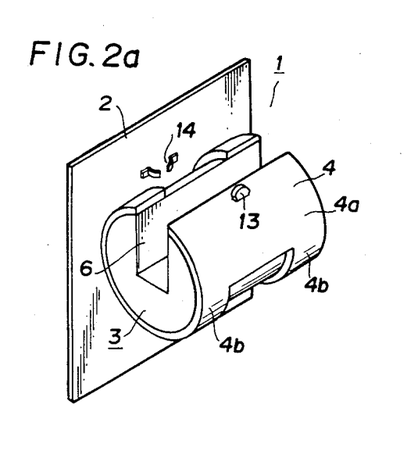
FIGS. 2a and 2b are perspective and plan views each showing another embodiment of the wire holder wherein the shape of a rotatable member differs from that of FIG. 1.
Figure 2B:
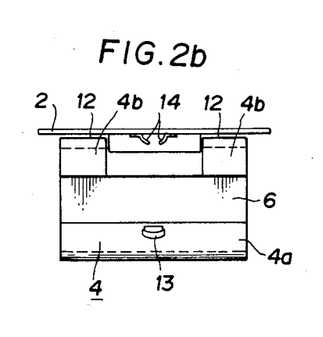
Figure 3A:
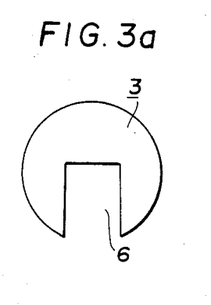
FIGS. 3a, 3b, 3c, 3d, 3e and 3f are explanatory views illustrating modifications to the structure of the bracket.
Figure 3B:
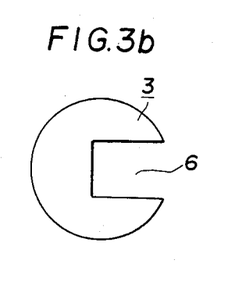
Figure 3C:
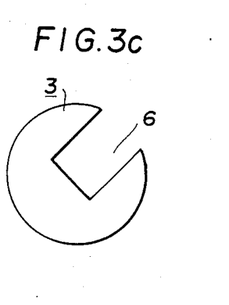
Figure 3D:
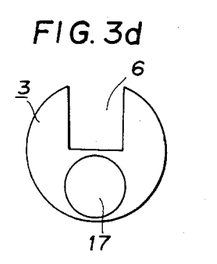
Figure 3E:
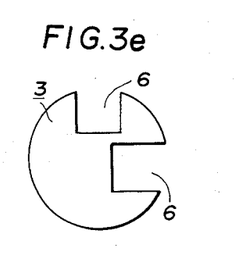
Figure 3F:
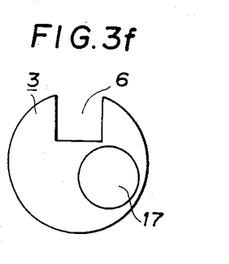

While the rotatable member 4 per FIG. 1 is constructed such that one body portion 4b extends from the central part of the cover portion 4a and the guide hole 12 is defined at the central position of the bracket 3, it may also be constructed, as shown in FIGS. 2a and 2b, such that a pair of body portions 4b extend from the opposite end portions of the cover portion 4a and guide holes 12 are defined at the opposite end portions of the bracket 3. The upwardly opened slot 6 is defined on the bracket 3 in FIGS. 1 and 2, respectively, but such a slot may also be defined such that it is downwardly opened as shown in FIG. 3a, it is opened sidewards as shown in FIG. 3b, or it is inclinedly opened in FIG. 3c dependent upon purposes of application. Furthermore, one polygonal slot 6 is provided in the above embodiments, but they are not limited thereto, and another circular inserting hole 17 may be defined on either the lower or side part of the bracket 3 as shown in FIG. 3d and FIG. 3f, and moreover two or more polygonal slots 6 may be defined on the bracket 3 as shown in FIG. 3e.

Figure 4A:
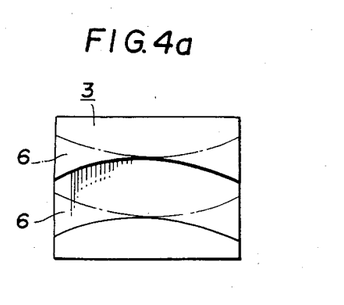
FIGS. 4a and 4b are explanatory views showing a construction of the bracket having a curved slot.
Figure 4B:
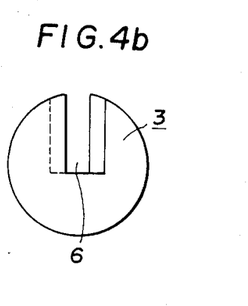

While the respective slots 6 in FIGS. 1, 2 and 3 are defined with straight lines, such slots may be inwardly curved with a prescribed radius of curvature as shown in FIGS. 4a and 4b. According to such construction, the arch wire 23 can be smoothly inserted into the slot 6. In this case, the slot 6 may optionally be outwardly curved as indicated by broken lines in FIG. 4a.

Figure 5A:
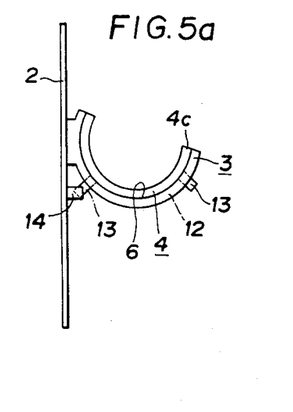
FIGS. 5a and 5b are explanatory views showing the wire holder according to the present invention comprising a bracket and a rotatable member each having a side profile of circular arc.
Figure 5B:
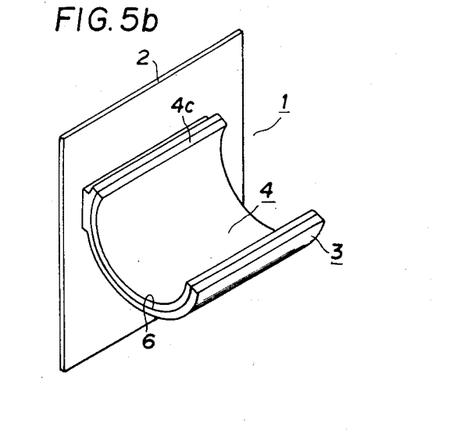

FIGS. 5a and 5b show an example of arch wire holder consisting of a bracket 3 formed by a sheet material (for example, plate-like member) and having a side profile of a circular arc (including C-shaped or semi-arcuated side profile) and a rotatable member 4 having also a side profile of circular arc which is rotatably supported by the inner circumferential surface of the bracket 3 fixed to a stationary base 2. More specifically, the bracket 3 has a side profile of circular arc to define the slot 6 within which the rotatable member 4 having substantially the same side profile as that of the bracket 3 is placed and the former is engaged with the latter. An operating projection 13 is protrusively formed on the circumferential surface of the rotatable member 4, and this projection 13 extends from a slit-like guide hole 12 punched on the bracket 3 along the direction of an outer diameter. An engaging member 14, similar to that of FIG. 1, is formed on the stationary base 2. Because of smooth rotation of the rotatable member 4, the slot 6 (the inner circumferential shape of the bracket 3) for holding an arch wire has the circumferential surface in the embodiment of FIG. 5. While the slot 6 is formed in straight line along the axial direction in FIG. 5, such a slot may be curved with a prescribed radius of curvature as in FIG. 4.

Figure 6A:
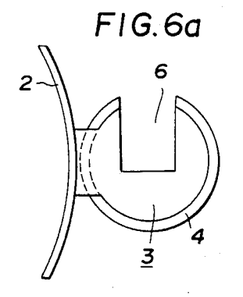
FIGS. 6a and 6b, as well as FIGS. 7a and 7b, are explanatory views illustrating modifications of stationary base, respectively.
Figure 6B:
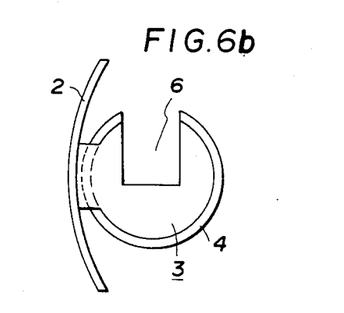
Figure 7A:
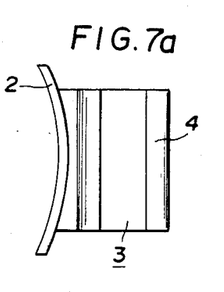
Figure 7B:
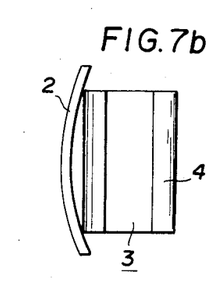

Furthermore FIGS. 6a and 6b as well as FIGS. 7a and 7b illustrate other embodiments of the stationary base 2, wherein stationary bases 2 of FIGS. 6a and 6b are respectively curved outwardly and inwardly viewed from the horizontal direction, whilst bases 2 of FIGS. 7a and 7b are curved outwardly and inwardly as viewed from the vertical direction. In addition, the bases 2 of FIGS. 6a and 6b may be combined with those of FIGS. 7a and 7b to obtain modifications of three-dimensionally curved stationary bases. Thus, such a stationary base may be variously modified dependent upon the configuration of teeth to be corrected, purposes of application and the like.

It is to be noted that shapes or configurations of such arch wire holder 1 comprising a bracket, a rotatable member and the like, as well as of such stationary base 2 as mentioned above, are not limited to those in the above embodiments, but various modifications can be made.

Because the above embodiments have been constructed such that the bracket is fixed to the stationary base and the rotatable member is rotatably supported by the outer or inner circumference of the bracket, for opening and closing the slot for receiving arch wire defined on the bracket, the operation by which the arch wire is inserted in and fixed to the bracket in a mouth can be carried out in a short period of time, so that its orthodontic effects can be improved. In addition, costs for such orthodontic appliance can be reduced, since the construction thereof is simple.

Figure 8A:
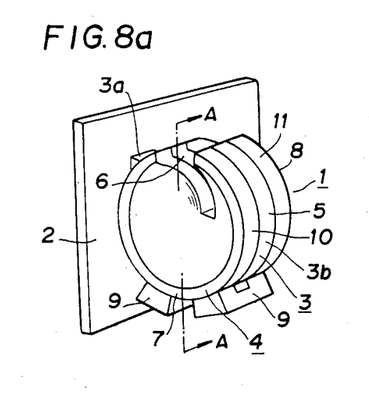
FIGS. 8a and 8b are, respectively, a perspective view illustrating another embodiment of the wire holder according to the present invention, and a partially sectional view taken along the line A—A.
Figure 8B:
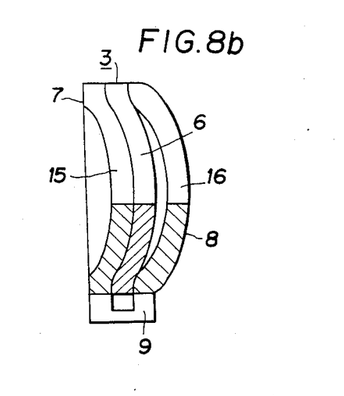
Figure 9:
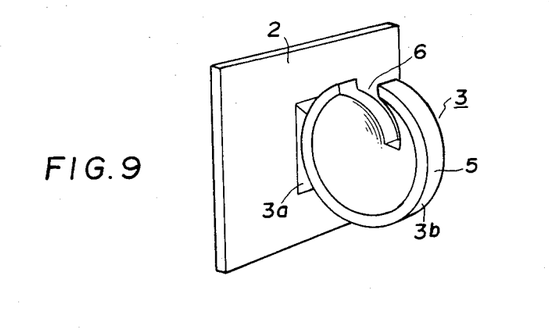
FIG. 9 is a perspective view showing a stationary base and a bracket.
Figure 10A:
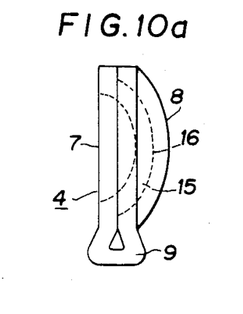
FIGS. 10a and 10b are side and perspective views showing a rotatable member, respectively.
Figure 10B:
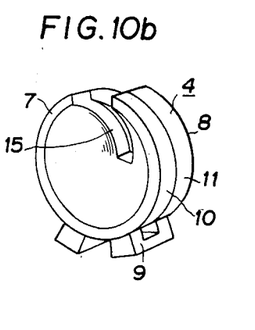
Figure 11:
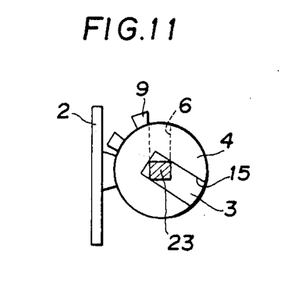
FIG. 11 is an explanatory view showing a state in which a wire is received by a slot.

Next, FIGS. 8a and 8b–FIG. 11 illustrate other embodiments of the present invention wherein an arch wire holder 1 for orthodontic appliance is composed of a stationary base 2 which is to be directly adhesive bonded to a tooth, a bracket 3 constructed integrally to the stationary base 2, and a rotatable member 4 provided with sandwiching members which are engaged with the opposite sides of the bracket 3, respectively. Like the stationary base 2, the tooth-band 24 as shown in FIG. 21 may be also used in addition to the bonding plate as shown in the present embodiment. As shown in FIGS. 8a, 8b and 9, the bracket 3 has a unitary construction consisting of a base portion 3a and a wire holding portion 3b provided with a slot 6 for receiving an arch wire and which is defined on a part extending from the outer circumference 5 of the wire holding portion 3b to a central portion thereof. Further, the central portion of the bracket 3 is curved towards either side thereof as shown in FIG. 8b. The rotatable member 4 is integrally constructed with a pair of the opposed sandwiching members 7 and 8 together with a spring member 9 for forcing the sandwiching members 7 and 8 in a direction so as to pressingly contact them with each other as shown in FIGS. 8a, 8b and FIGS. 10a, 10b. The respective sandwiching members 7 and 8 possess notched portions 15 and 16 being capable of communicating with the slot 6 of the bracket 3, and the central portions of both the sandwiching members 7 and 8 are curved towards a side thereof in such a manner that convex of the inside (right side) of central curved portion in the sandwiching member 7 conforms with convex of the outside (left side) of the central curved portion in the bracket 3 (in this case, complete contact over the whole surfaces of both the members is not necessarily required), whilst convex of the inside (left side) of the central curved portion in the sandwiching member 8 conforms to convex of the outside (right side) of the bracket 3 (in this case, complete contact over the whole surfaces of both the sandwiching member and the bracket is not necessarily required). The spring member 9 forces both the sandwiching members 7 and 8 in each direction along which the member 7 or 8 contacts pressingly to the bracket 3 with such an extent that both the sandwiching members 7 and 8 are rotatable around the center of the central curved portion of the bracket 3 (as the rotating shaft) in frictionally slidable manner, when the sandwiching members 7 and 8 are forcibly attached to the opposite sides of the bracket 3, respectively, as shown in FIGS. 8 and 8b.

In the course of rotating the rotatable member 4, when the notched portions 15 and 16 reach a position where they communicate wholly with the slot 6 of the bracket 3 (opened position), a wire 23 is insertable, and the respective sandwiching members 7 and 8 are further rotated from the opened position while maintaining such a state that the wire 23 has been seated at the bottom of the slot 6, so that the wire 23 is held by the inner walls (including the bottom) of the slot 6 as well as the inner walls (including both the bottoms) of the notched portions 15 and 16 in the sandwiching members 7 and 8, whereby the wire 23 is positively captured by the wire holder 1.

This type of the arch wire holder 1 is constructed such that the rotatable member 4 cannot be rotated so far as external force is applied along the rotating direction of the rotatable member 4 due sandwiching of the bracket 3 between both the members 7 and 8 by means of elastic force of the spring member 9. In this case, it is not required that the engaging surfaces between the bracket 3 and the respective sandwiching members 7 and 8 make contact completely with each other over the whole surfaces thereof, hence partial contact may be permitted if there is a contacting force of such a magnitude that the respective sandwiching members 7 and 8 are not easily rotated when external force is not applied in the rotating direction thereof.

Figure 12:
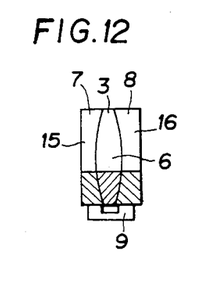
FIGS. 12, 13, 14 and 15 are explanatory views illustrating modifications of FIG. 8 in the vertical section, respectively.

FIG. 12 is a sectional view illustrating another embodiment of the arch wire holder according to the present invention which is different from the embodiment of FIG. 8 in that the opposite sides of the bracket 3 define wholly convex profiles, and each inside surface of the sandwiching members 7 and 8 engaging with the aforesaid convex profiles defines a concave profile.

Figure 13:
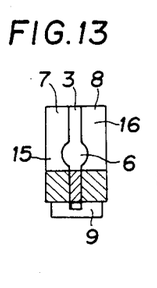

FIG. 13 is a sectional view showing still another embodiment of the arch wire holder of the present invention which is different from the above described respective embodiments in that the central portion in the opposite sides of the bracket 3 defines an outwardly projecting convex profile, whilst a central portion of each inside surface of the sandwiching members 7 and 8 engaging with the above convex profile defines a matching concave profile.

Figure 14:
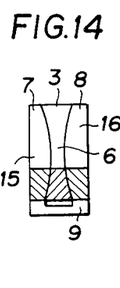

FIG. 14 is a sectional view showing yet another embodiment of the arch wire holder of the invention which is different from the aforesaid respective embodiments in that the opposite sides of the bracket 3 define wholly concave profile, whilst the corresponding portion of each inside surface of the sandwiching members 7 and 8 engaging with said concave profile defines a corresponding convex profile.

Figure 15:
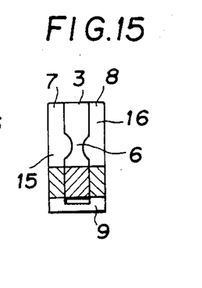

FIG. 15 is a sectional view illustrating a further embodiment of the arch wire holder according to the invention which is different from the respective abovementioned embodiments in that the central portion in the opposite sides of the bracket 3 defines a concave profile, whilst a central portion of each inside surface of the sandwiching members 7 and 8 engaging with said concave profile defines a corresponding convex profile.

Figures 16A, 16B:
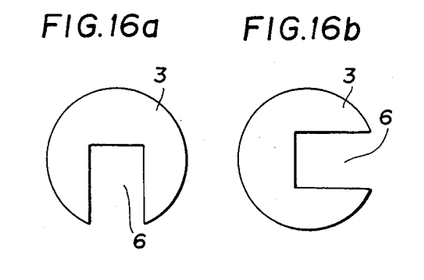
FIGS. 16a, 16b and 16c are explanatory views showing constructions of brackets wherein each position of a slot to be defined is varied, respectively.
Figure 16C:
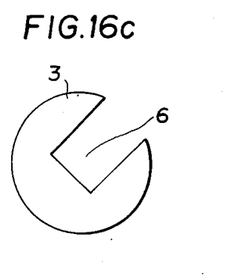

The slot 6 of each bracket 3 is defined at the upper part of the bracket 3 in FIGS. 8 to 15, but such slot may be also defined at the lower part of the bracket 3 as in FIG. 16a and at the side part of the bracket 3 as in FIG. 16b, or it may be inclinedly defined in the bracket 3 as in FIG. 16c, dependent upon the purposes of application.

Figure 17A:
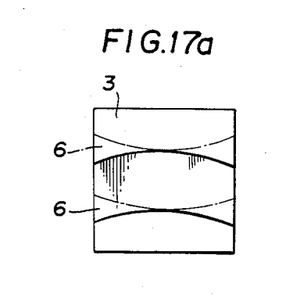
FIGS. 17a and 17b are explanatory views showing a construction of the bracket having a curved slot, respectively.
Figure 17B:
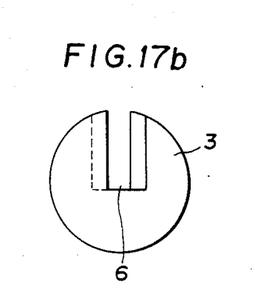

While the respective slots 6 in FIGS. 8–16 are defined with straight lines, such a slot may be inwardly curved with a prescribed radius of curvature as shown in FIGS. 17a and 17b and, according to such a construction, the arch wire 23 can be smoothly inserted into the slot 6. Furthermore the slot 6 may outwardly be curved as indicated by the chain line in FIG. 17a, but in this case the profiles of both the sandwiching members must be curved so as to conform to the curved profile of the slot 6 when the former profiles are superposed completely upon the latter profile.

Figure 18:
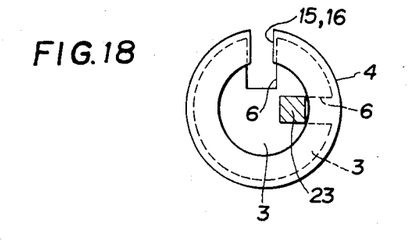
FIG. 18 is an explanatory view illustrating another embodiment of the wire holder according to the present invention.

FIG. 18 illustrates an yet further embodiment of the arch wire holder of this invention wherein two groove-like slots 6 are defined on the outer circumference of a cylindrical bracket 3 with a prescribed distance, whilst single notched portions 15 and 16, each capable of communicating with said respective slots 6, are defined on the ring-shaped sandwiching members of a rotatable member 4. In this construction of the wire holder, a wire 23 is held by the bottom of either slot 6 as well as the inner circumferential surfaces of the ring-shaped sandwiching members 15 and 16. according to the present embodiment, it is advantageous that a plurality of different wire fixing states can be attained by one wire holder. It is to be noted that the position for defining a slot or slots and number thereof are not limited to those illustrated in FIG. 18.

Figure 19A:
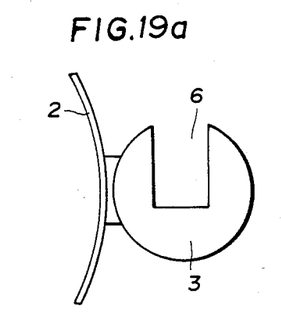
FIGS. 19a and 19b, as well as FIGS. 20a and 20b, are explanatory views illustrating modifications of the stationary base to be used for the wire holders shown in FIGS. 8–18.
Figure 19B:
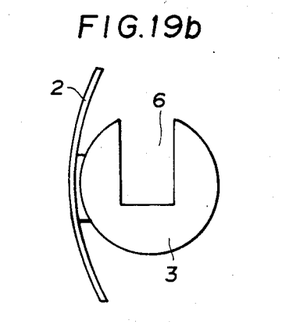
Figure 20A:
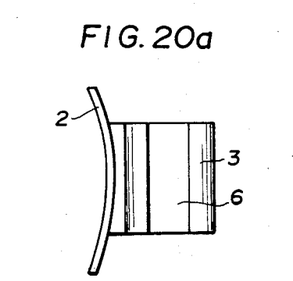
Figure 20B:
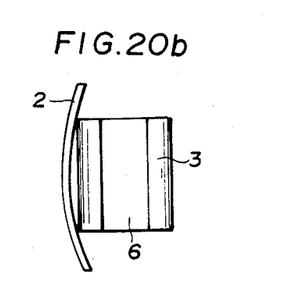

Furthermore, FIGS. 19a and 19b, as well as FIGS. 20a and 20b, illustrate other embodiments of the stationary base 2, respectively, wherein stationary bases 2 of FIGS. 19a and 19b are ones curved outwardly and inwardly viewed from the horizontal direction, while the bases 2 of FIGS. 20a and 20b are ones curved outwardly and inwardly viewed from the vertical direction. In addition, the stationary bases 2 of FIGS. 19a and 19b may be combined with those of FIGS. 20a and 20b to obtain modifications of three-dimensionally curved stationary bases. Thus, such stationary bases may be variously modified dependent upon the configuration of teeth to be corrected, purposes of application and like.

It is to be noted that shapes or configurations of such an arch wire holder, comprising a bracket, sandwiching members and the like, as well as such stationary bases as mentioned above, are not limited to those disclosed explicitly in the above embodiments, but various modifications thereof can be realized.

The orthodontic appliance according to the present invention may be attached to the front (buccal) side of teeth as shown in FIG. 21, and in the same way it may also be attached to the rear (lingual) side of teeth as shown in FIG. 22.

According to the orthodontic appliance of the present invention as described above, attachment and detachment of an arch wire can easily and positively be effected by a one-shot operation so that the time required for dental treatment can be reduced, medical accidents can be prevented, and force for correcting irregularities in teeth can be positively transferred to required positions, thus providing significant advantages for dental patients. In addition, since the shape or configuration of each part constituting the orthodontic appliance is simple, the manufacture of the same is easy so that the manufacturing cost can be reduced.

Other modifications of the present invention may occur to those skilled in the art based upon a reading of the present disclosure and such are intended to be included within the scope of the following claims.

I claim:

1. An orthodontic appliance wherein a plurality of wire holders is affixed, one to a tooth in a dental patient's mouth, and at least one correcting arch wire is engaged with said wire holders for applying corrective forces to irregular teeth, comprising:
   a wire holder having a base for affixation to a tooth;
   a bracket attached to said base and provided with at least one slot for receiving said arch wire therein, said bracket also being shaped in a first part to be generally normal to the attached tooth, said part having a curved profile; and
   an arch wire locking member shaped in substantial portion as a connected pair of thin segments shaped to closely and slidably sandwich and hence be rotatably supported by said curved first part of said bracket, each of said pair of sandwiching members having formed therein a locking slot corresponding in a first open position of said locking member to said slot in said bracket for placement in or removal of said arch wire in said slot in said bracket and said locking member being rotatable to a second locking position wherein said arch wire becomes securely retained within said slot in said bracket.

2. An orthodontic appliance as claimed in claim 1, wherein:
   said connected pair of this segments of said locking member are biased towards each other so as to exert a gripping force on said bracket sandwiched therebetween.

3. An orthodontic appliance as claimed in claim 1, wherein: at least a fraction of each of the curved opposite sides of said first part of said bracket is convex and the inner side of each one of said respective sandwiching segments has a matching contacting concave profile.

4. An orthodontic appliance as claimed in claim 3, wherein: the whole surface of each of the curved opposite sides of said first part of said bracket is convex.

5. An orthodontic appliance as claimed in claim 1, wherein: at least a fraction of each of the curved opposite sides of said first part of said bracket is concave and the inner side of each one of said respective sandwiching segments has a matching contacting convex profile.

6. An orthodontic appliance as claimed in claim 5, wherein: the whole surface of each of the curved opposite sides of said first part of said bracket is concave.

7. An orthodontic appliance as claimed in claim 1, wherein: each sandwiching segment of said rotatable locking member is formed into a ring-form, and said arch wire is held by a spacing defined between the bottom of the slot in said bracket and the inner circumferential surfaces of said ring-form sandwiching segments when said rotatable locking member is in said locked position.

8. An orthodonic appliance, wherein a plurality of wire holders is affixed one to a tooth in a dental patient's mouth and at least one correcting arch wire is engaged with said wire holders for applying corrective forces to irregular teeth, comprising:
   a wire holder having a base for affixation to a tooth;
   a bracket attached to said base and provided with at least one slot for receiving said arch wire therein;
   an arch wire locking member rotatably supported along a first portion by said bracket such that in a first predetermined position of said locking member said arch wire may be freely received in said slot or removed therefrom and said locking member has a second predetermined locked position to securely retain said arch wire within said slot; and
   locking means integral with said wire holder for positively engaging a second portion of said locking member for secure locking thereof in said second locked position thereby to ensure secure retention of said arch wire in said slot;
   wherein said bracket has a laterally cylindrical portion provided with said slot having a polygonal cross-section and extending along said cylinder's axial direction, and said locking member is rotatably engaged with the outer cylindrical surface of said bracket so that an opening of said slot at said cylindrical surface is closed to capture said arch wire inserted in said slot when said locking member is in said second position, and said opening of said slot is opened to permit said wire to be received in or removed from said slot when said locking member is rotated to said first position, and said cylindrical portion of said bracket is also provided with an aperture for holding a wire inserted through said bracket along said axial direction.

9. An orthodonic appliance, wherein a plurality of wire holders is affixed one to a tooth in a dental patient's mouth and at least one correcting arch wire is engaged with said wire holders for applying corrective forces to irregular teeth, comprising:
   a wire holder having a base for affixation to a tooth;
   a bracket attached to said base and provided with at least one slot for receiving said arch wire therein, said slot having a pair of opposed inner walls curved unidirectionally;
   an arch wire locking member rotatably supported along a first portion by said bracket such that in a first predetermined position of said locking member said arch wire may be freely received in said slot or removed therefrom and said locking member has a second predetermined locked position to securely retain said arch wire within said slot; and
   locking means integral with said wire holder for positively engaging a second portion of said locking member for secure locking thereof in said second locked position thereby to ensure secure retention of said arch wire in said slot.

* * * * *